United States Patent [19]
Stanton et al.

[11] Patent Number: 5,155,130
[45] Date of Patent: Oct. 13, 1992

[54] CERTAIN BENZOPYRAN AND BENZOTHIOPYRAN DERIVATIVES

[75] Inventors: James L. Stanton, Lebanon; Yoshitaka Satoh, Scotch Plains, both of N.J.; Alan J. Hutchison, Madison, Conn.

[73] Assignee: Ciba-Geigy Corporation, Ardsley, N.Y.

[21] Appl. No.: 595,153

[22] Filed: Oct. 10, 1990

Related U.S. Application Data

[63] Continuation-in-part of Ser. No. 392,510, Aug. 11, 1989, abandoned.

[51] Int. Cl.$^5$ .................. A61K 31/35; C07D 311/66; C07D 311/58
[52] U.S. Cl. ................... 514/456; 549/407; 549/405; 549/23
[58] Field of Search ................ 549/405, 407; 514/456

[56] References Cited

U.S. PATENT DOCUMENTS

| | | | |
|---|---|---|---|
| 4,305,955 | 12/1981 | Belletire | 424/275 |
| 4,486,428 | 12/1984 | Eggler et al. | 424/248.4 |
| 4,738,986 | 4/1988 | Kneen et al. | 514/575 |
| 4,792,560 | 12/1988 | Huang | 514/311 |
| 4,801,605 | 1/1989 | Hutchison | 514/432 |
| 4,873,259 | 10/1989 | Summers, Jr. et al. | 514/443 |

FOREIGN PATENT DOCUMENTS

| | | |
|---|---|---|
| 218373 | 4/1987 | European Pat. Off. . |
| 292699 | 4/1988 | European Pat. Off. . |
| 313295 | 10/1988 | European Pat. Off. . |
| 313296 | 10/1988 | European Pat. Off. . |
| 408760A1 | 1/1991 | European Pat. Off. . |
| WO8704152 | 7/1987 | PCT Int'l Appl. . |
| WO9007494 | 7/1990 | PCT Int'l Appl. . |

OTHER PUBLICATIONS

Eur. J. Med. Chem. 22, 539 (1987).
Indian J. Chemistry 21B, 344 (1982).
Eur. J. Med. Chem.-Chim. Ther. 1982, 577–581.
J. Chem. Soc. Perkin Trans. II, 1247 (1988).
J. Chem. Soc. Perkin Trans. I, 197 (1983).
J. Med. Chem. 1988, 31, 3–5.

*Primary Examiner*—Nicky Chan
*Attorney, Agent, or Firm*—Norbert Gruenfeld

[57] ABSTRACT

The invention relates to the compounds of the formula

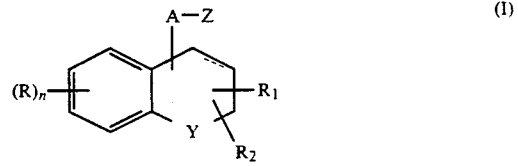

wherein each R independently represents hydrogen, lower alkyl, halogen, trifluoromethyl, lower alkoxy, carbocyclic or heterocyclic aryl, carbocyclic or heterocyclic aryloxy, carbocyclic or heterocyclic aryl-lower alkyloxy, carbocyclic or heterocyclic aryl-lower alkyl, $C_3$–$C_7$-cycloalkyl-lower alkyloxy, or $C_3$–$C_7$-cycloalkyloxy; $R_1$ represents hydrogen, lower alkyl or carbocyclic aryl; $R_2$ represents hydrogen or lower alkyl; Y represents oxygen (O), sulfur (S), sulfinyl or sulfonyl; n represents 1, 2 or 3; A represents a direct bond or lower alkylene; Z represents

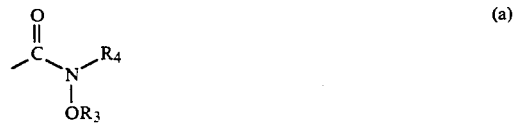

wherein $R_3$ represents hydrogen or acyl; $R_4$ represents lower alkyl, $C_3$–$C_7$-cycloalkyl, carbocyclic or heterocyclic aryl, carbocyclic or heterocyclic aryl-lower alkyl, or $C_3$–$C_7$-cycloalkyl-lower alkyl; or Z represents

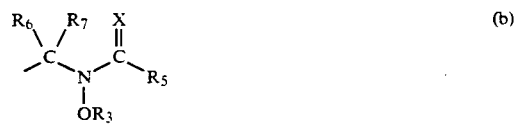

wherein X represents oxygen or sulfur, $R_3$ represents hydrogen, acyl, lower alkoxycarbonyl, aminocarbonyl, mono- or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylamino-carbonyl; $C_3$–$C_7$-cycloalkylaminocarbonyl, or $C_3$–$C_7$-cycloalkyl-lower alkylaminocarbonyl; $R_5$ represents lower alkyl, lower alkoxycarbonyl-lower alkyl, $C_3$–$C_7$-cycloalkyl, carbocyclic or heterocyclic aryl, carbocyclic or heterocyclic aryl-lower alkyl, $C_3$–$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$–$C_7$-cycloalkylamino, $C_3$–$C_7$-cycloalkyl-lower alkylamino, lower alkoxycarbonyl-lower alkylamino, or lower alkoxy; $R_6$ and $R_7$ independently represent hydrogen or lower alkyl; and pharmaceutically acceptable salts thereof; which are useful as 5-lipoxygenase inhibitors.

11 Claims, No Drawings

CERTAIN BENZOPYRAN AND BENZOTHIOPYRAN DERIVATIVES

CROSS REFERENCE TO RELATED APPLICATIONS

This application is a continuation-in-part of application Ser. No. 392,510 filed Aug. 11, 1989, now abandoned.

SUMMARY OF THE INVENTION

The invention relates to the benzopyran and benzothiopyran derivatives as defined herein which are particularly useful as selective lipoxygenase inhibitors, methods for preparation thereof, pharmaceutical compositions comprising said compounds, and a method of inhibiting lipoxygenase, in particular 5-lipoxygenase, and of treating diseases in mammals which are responsive to lipoxygenase inhibition using said compounds or pharmaceutical compositions comprising said compounds of the invention.

The compounds of the invention are particularly useful for the prevention and treatment of various inflammatory and allergic conditions, e.g. bronchial allergies and inflammatory disorders such as asthma, allergic rhinitis (hay fever), ocular allergies and inflammation, inflammatory bowel disease (including Crohn's disease, ulcerative colitis), and dermatological allergies and inflammation such as eczema and psoriasis; also for the treatment of rheumatic disorders such as rheumatoid arthritis, osteoarthritis and gouty arthritis; also for the treatment of ischemic conditions such as myocardial infarction and cerebral ischemia; also for the treatment of multiple sclerosis; for the treatment of endotoxin shock; for the treatment of renal disorders, such as primary nephrotic syndrome and cyclosporine-induced renal toxicity; in the treatment of certain carcinomas, e.g. to inhibit tumor metastasis; also to inhibit gastrointestinal side effects of non-steroidal antiinflammatory drugs.

DETAILED DESCRIPTION OF THE INVENTION

More particularly the invention relates to the compounds of formula I

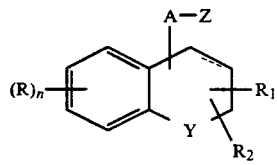

(I)

wherein each R independently represents hydrogen, lower alkyl, halogen, trifluoromethyl, lower alkoxy, carbocyclic or heterocyclic aryl, carbocyclic or heterocyclic aryloxy, carbocyclic or heterocyclic aryl-lower alkyloxy, carbocyclic or heterocyclic aryl-lower alkyl, $C_3$-$C_7$-cycloalkyl-lower alkyloxy, or $C_3$-$C_7$-cycloalkyloxy; $R_1$ represents hydrogen, lower alkyl or carbocyclic aryl; $R_2$ represents hydrogen or lower alkyl; Y represents oxygen (O), sulfur (S), sulfinyl or sulfonyl; n represents 1, 2 or 3; A represents a direct bond or lower alkylene; Z represents

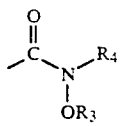

(a)

wherein $R_3$ represents hydrogen or acyl; $R_4$ represents lower alkyl, $C_3$-$C_7$-cycloalkyl, carbocyclic or heterocyclic aryl, carbocyclic or heterocyclic aryl-lower alkyl, or $C_3$-$C_7$-cycloalkyl-lower alkyl; or Z represents

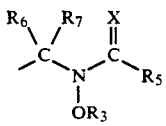

(b)

wherein X represents oxygen or sulfur, $R_3$ represents hydrogen, acyl, lower alkoxycarbonyl, aminocarbonyl, mono- or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3$-$C_7$-cycloalkylaminocarbonyl, or $C_3$-$C_7$-cycloalkyl-lower alkylaminocarbonyl; $R_5$ represents lower alkyl, lower alkoxycarbonyl-lower alkyl, $C_3$-$C_7$-cycloalkyl, carbocyclic or heterocyclic aryl, carbocyclic or heterocyclic aryl-lower alkyl, $C_3$-$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$-$C_7$-cycloalkylamino, $C_3$-$C_7$-cycloalkyl-lower alkylamino, lower alkoxycarbonyl-lower alkylamino, or lower alkoxy; $R_6$ and $R_7$ independently represent hydrogen or lower alkyl; and pharmaceutically acceptable salts thereof.

The dotted line in formula I and further formulae herein denotes that the bond between the respective carbon atoms at positions 3 and 4 of the benzopyran or benzothiopyran ring system represents either a single or a double bond, as is conventional in the art. Said compounds with a single bond are represented by formula I in which the dotted line is absent. Said compounds with a double bond are represented by formula I in which the dotted line is replaced by a solid line.

The double bond may also be located between carbon atoms at positions 2 and 3 of the benzopyran or benzothiopyran ring system and such compounds are also within the purview of the invention.

One or more of the substituents represented by $(R)_n$ as defined above may be located at positions 5, 6, 7 or 8 of the ring system, n being preferably one or two, and advantageously one preferably located at the 6-position. The grouping A-Z may be located at positions 2, 3 or 4, preferably position 3. $R_1$ and $R_2$ may also be located at available positions on carbon atoms 2, 3 or 4, $R_1$ and $R_2$ being on the same carbon atom or on different carbon atoms.

Particular embodiments of the invention relate to compounds wherein Z represents either group (a) or (b).

A preferred embodiment of the invention relates to the compounds of formula II

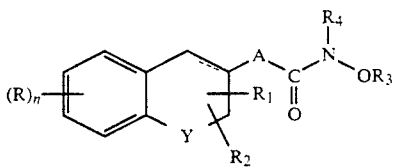

wherein n, R, $R_1$–$R_4$, A and Y have meaning as defined above; and pharmaceutically acceptable salts thereof.

Another preferred embodiment of the invention relates to the compounds of formula III

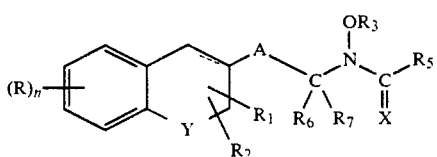

wherein n, R, $R_1$–$R_3$, $R_5$–$R_7$, A, X and Y have meaning as defined above; and pharmaceutically acceptable salts thereof.

Further particular embodiments of the invention are also directed to compounds of formula I, II and III wherein either Y represents oxygen (O) or Y represents sulfur (S), sulfinyl or sulfonyl respectively; also wherein the bond between carbon atoms at positions 3 and 4 either represents a single bond or a double bond.

Preferred are the compounds of formula I, II or III wherein A represents a direct bond. Also preferred are the compounds wherein $R_3$ represents hydrogen, the compounds having a double bond between carbon atoms at positions 3 and 4, the compounds wherein $R_1$ and $R_2$ are at position 2, and the compounds of formula I and III wherein X represents oxygen; also the compounds of formula I and III wherein X and Y represent oxygen and $R_5$ represents amino or substituted amino as defined for $R_5$.

Preferred are said compounds of formula II wherein n represents 1 or 2; Y represents oxygen or sulfur; A represents a direct bond; R represents hydrogen, lower alkoxy, halogen, lower alkyl, carbocyclic or heterocyclic aryl-lower alkyloxy, or carbocyclic or heterocyclic aryloxy; $R_1$ represents hydrogen, lower alkyl or carbocyclic aryl; $R_2$ represents hydrogen or lower alkyl; $R_3$ represents hydrogen or acyl; $R_4$ represents lower alkyl; and pharmaceutically acceptable salts thereof.

Further preferred are the compounds of formula II wherein n represents 1; Y represents oxygen or sulfur; A represents a direct bond; R represents hydrogen, lower alkoxy, lower alkyl, carbocyclic aryl-lower alkyloxy or carbocyclic aryloxy; $R_1$ and $R_2$ represent hydrogen or lower alkyl; $R_3$ represents hydrogen or lower alkanoyl; $R_4$ represents lower alkyl; and pharmaceutically acceptable salts thereof.

Preferred compounds of formula II are those of formula IV

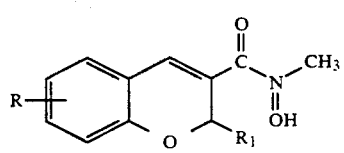

wherein R represents hydrogen, lower alkyl, lower alkoxy, carbocyclic aryl-lower alkyloxy or carbocyclic aryloxy; $R_1$ represents hydrogen, lower alkyl or carbocyclic aryl; and pharmaceutically acceptable salts thereof; also dihydro derivatives thereof wherein the bond between the carbon atoms at positions 3 and 4 is a single bond.

Also preferred are the compounds of formula III wherein n represents 1 or 2; Y represents oxygen or sulfur; X represents oxygen; A represents a direct bond; R represents hydrogen, lower alkoxy, halogen, lower alkyl, carbocyclic or heterocyclic aryl-lower alkyloxy or carbocyclic or heterocyclic aryloxy; $R_1$ represents hydrogen, lower alkyl or carbocyclic aryl; $R_2$ represents hydrogen or lower alkyl; $R_3$ represents hydrogen or acyl; $R_5$ represents lower alkyl, amino, mono-lower alkylamino or mono-carbocyclic arylamino; $R_6$ and $R_7$ independently represent hydrogen or lower alkyl; and pharmaceutically acceptable salts thereof.

Further preferred are the compounds of formula III wherein n represents 1; X represents oxygen; Y represents oxygen or sulfur; A represents a direct bond; R represents hydrogen, lower alkoxy, lower alkyl, carbocyclic aryl-lower alkyloxy or carbocyclic aryloxy; $R_1$ and $R_2$ independently represent hydrogen or lower alkyl; $R_3$ represents hydrogen or acyl, preferably lower alkanoyl; $R_5$ represents lower alkyl, amino, mono-lower alkylamino or mono-carbocyclic arylamino; $R_6$ represents hydrogen or lower alkyl; $R_7$ represents hydrogen; and pharmaceutically acceptable salts thereof.

Also preferred are the hereinabove compounds of formula III wherein $R_3$ represents aminocarbonyl, lower alkylaminocarbonyl or carbocyclic arylaminocarbonyl; $R_5$ represents amino, lower alkylamino or carbocyclic arylamino; and n, X, Y, A, $R_1$, $R_2$, $R_6$ and $R_7$ have meaning as defined above; and pharmaceutically acceptable salts thereof.

Particularly preferred compounds of formula III are those of formula V

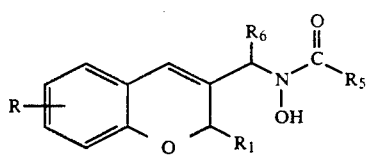

wherein R represents hydrogen, lower alkyl, lower alkoxy, carbocyclic aryl-lower alkyloxy or carbocyclic aryloxy; $R_1$ represents hydrogen, lower alkyl or carbocyclic aryl; $R_6$ represents hydrogen or lower alkyl; $R_5$ represents mono-lower alkylamino, mono-carbocyclic arylamino or amino; and pharmaceutically acceptable salts thereof.

Further preferred are compounds of formula V wherein R represents carbocyclic aryloxy; $R_1$ and $R_6$ independently represent hydrogen, methyl or ethyl; and $R_5$ represents mono-$C_1$–$C_3$-alkylamino, mono-carbocyclic arylamino or amino; and pharmaceutically acceptable salts thereof.

A further aspect of the hereinabove cited compounds of formula III are the compounds of formula Va

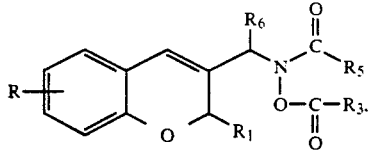

(Va)

wherein R represents hydrogen, lower alkyl, lower alkoxy, carbocyclic aryl-lower alkyloxy or carbocyclic aryloxy; $R_1$ represents hydrogen, lower alkyl or carbocyclic aryl; $R_3'$ and $R_5$ are identical and represent mono-lower alkylamino, mono-carbocyclic arylamino or amino; $R_6$ represents hydrogen or lower alkyl; and pharmaceutically acceptable salts thereof.

Also preferred are the dihydro derivatives of said compounds of formula V and Va wherein the bond between the carbon atoms at positions 3 and 4 is a single bond.

In the above cited compounds, a substituent R is preferably attached to the 6 or 7 position of the benzopyran or benzothiopyran ring, advantageously at the 6-position.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1-4 carbon atoms, advantageously 1-3 carbon atoms, and represents for example ethyl, propyl, butyl or most advantageously methyl.

A lower alkenyl group, as in lower alkenylamino, is preferably bonded on a saturated carbon. Such group preferably has 3-7, advantageously 3 or 4 carbon atoms and is e.g. allyl.

A lower alkynyl group, as in lower alkynylamino, is preferably bonded on a saturated carbon. Such group preferably has 3-7, advantageously 3 or 4 carbon atoms and is e.g. propargyl.

A lower alkoxy (or alkyloxy) group preferably contains 1-4 carbon atoms, advantageously 1-3 carbon atoms, and represents for example methoxy, ethoxy, propoxy or isopropoxy.

Halogen preferably represents chloro or fluoro but may also be bromo or iodo.

Aryl represents carbocyclic or heterocyclic aryl.

Carbocyclic aryl represents for example phenyl or phenyl mono- or di-substituted by one or two radicals selected from lower alkyl, lower alkoxy, halogen, cyano and trifluoromethyl; or 1- or 2-naphthyl. Preferred it is phenyl or phenyl monosubstituted by halogen or trifluoromethyl.

Heterocyclic aryl represents for example pyridyl, quinolyl or thienyl, or any said radical substituted by lower alkyl or halogen. Pyridyl represents 2-, 3- or 4-pyridyl, advantageously 2- or 3-pyridyl. Thienyl represents 2- or 3-thienyl, advantageously 2-thienyl. Quinolyl represents preferably 2-, 3- or 4-quinolyl, advantageously 2-quinolyl.

Carbocyclic aryl-lower alkyl represents preferably straight chain or branched aryl-$C_1$-$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above.

Heterocyclic aryl-lower alkyl represents preferably straight chain or branched heterocyclic aryl-$C_1$-$C_4$-alkyl in which heterocyclic aryl has meaning as defined above, e.g. 2-, 3- or 4-pyridylmethyl or (2-, 3- or 4-pyridyl)-(ethyl, propyl or butyl); or 2- or 3-thienylmethyl or (2- or 3-thienyl)-(ethyl, propyl or butyl); and the like.

Similarly the terms carbocyclic aryl, heterocyclic aryl, lower alkyl, lower alkenyl, lower alkynyl have meaning as defined above in any groups in which such appear, e.g. aryloxy, aryl-lower alkyloxy and the like.

Acyl is preferably lower alkanoyl or aroyl.

Lower alkanoyl represents preferably $C_2$-$C_4$-alkanoyl such as acetyl or propionyl.

Aroyl represents preferably benzoyl or benzoyl mono- or di-substituted by one or two radicals selected from lower alkyl, lower alkoxy, halogen, cyano and trifluoromethyl; or 1- or 2-naphthoyl.

Lower alkoxycarbonyl represents preferably $C_1$-$C_4$-alkoxycarbonyl, e.g. ethoxy.

Substituted amino represents preferably mono-lower alkylamino or mono-carbocyclic arylamino.

$C_3$-$C_7$-Cycloalkyl represents cyclopropyl, cyclobutyl, cyclopentyl, cyclohexyl or cycloheptyl, preferably cyclohexyl or cyclopentyl.

Lower alkylene represents either straight chain or branched $C_1$-$C_7$-alkylene and represents preferably a methylene, ethylene, propylene or butylene chain, or said methylene, ethylene, propylene or butylene chain mono-substituted by $C_1$-$C_3$-alkyl or disubstituted on the same or different carbon atoms by $C_1$-$C_3$-alkyl (advantageously methyl), the total number of carbon atoms being up to and including 7.

Pharmaceutically acceptable salts of the acidic compounds of the invention (provided that $R_3$ represents hydrogen) are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, e.g. hydrochloric acid, are also possible provided a basic group, such as pyridyl, constitutes part of the structure.

The compounds of the invention exhibit valuable pharmacological properties in mammals, and are particularly useful as selective 5-lipoxygenase inhibitors for the treatment of e.g. inflammatory, allergic and ischemic conditions.

The above-cited properties are demonstrable in in vitro and in vivo tests, using advantageously mammals, e.g. rats, guinea pigs, dogs, rabbits or isolated organs, tissues, and enzyme preparations thereof, as well as cells and fluids isolated from mammalian, including human, blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-8}$ molar concentrations. The dosage in vivo may range, depending on the route of administration, between about 0.01 and 30 mg/kg.

5-HETE and various leukotriene products are formed from arachidonic acid by means of the enzyme 5-lipoxygenase. Leukotrienes (LTs) $B_4$, $C_4$, $D_4$ and $E_4$ are a group of mediators with potent leukocyte-chemoattractant, smooth muscle-constricting and vascular permeability-enhancing properties. $LTB_4$ is among the most potent leukocyte chemotactic agents known. $LTC_4$, $LTD_4$ and $LTE_4$ are components of the "slow-reacting substance of anaphylaxis" (SRS-A) and are potent inducers of broncho-constriction that are released during an antigen challenge in lungs. Leukotrienes have been implicated in the pathogenesis of a variety of vascular and pulmonary disorders involving leukocyte and smooth muscle activation. Since these products are derived from the biotransformation of arachidonic acid (AA) through the 5-lipoxygenase pathway, inhibition of 5-lipoxygenase will suppress biosynthesis of leukotrienes in leukocytes and various organ systems.

Beneficial effects are evaluated in pharmacological tests generally known in the art, e.g. as illustrated herein.

5-Lipoxygenase inhibition is determined e.g. by measuring the percent inhibition of the synthesis of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, essentially according to radiometric thin-layer chromatographic assays described by Walker and Dawson (J. Pharm. Pharmacol. 31: 778, 1979) and Jakschik and Lee (Nature 287: 51, 1980) to measure the formation of 5-HETE and $LTB_4$-like products from $^{14}C$-arachidonic acid. $IC_{50}$ values are determined graphically as the concentration of test compound at which the synthesis of 5-HETE and $LTB_4$-like products is reduced to 50% of their respective control values.

The inhibition of $LTB_4$ formation can also be determined in vitro in whole blood from dogs. One ml samples of blood are preincubated at 37° C. for 5 minutes with the desired concentration of test compound added as a solution in 10 microliters of dimethylsulfoxide. $LTB_4$ synthesis is then stimulated by the addition of A-23187 and N-formyl-met-leu-phe (f-MLP). The amount of $LTB_4$ is measured in the separated plasma fraction by radioimmunoassay. $IC_{50}$ values are determined graphically as the concentration of test compound causing 50% inhibition of $LTB_4$ formation seen in control whole blood.

Furthermore, the inhibition of 5-lipoxygenase is determined after oral or i.v. administration to rats or dogs by measuring ex vivo in whole blood the decrease of A-23187-stimulated $LTB_4$ formation as compared to non-treated control animals.

Antiinflammatory activity is demonstrated by measuring the inhibition of the edema and inhibition of the influx of polymorphonuclear (PMN's) and mononuclear leukocytes (monocytes and macrophages) after oral administration in the rat model in which pleurisy is first induced by injecting carrageenin into the pleural cavity, e.g. according to A. P. Almeida et al., J. Pharmacol. Exp. Therap. 214, 74 (1980), in particular during the late phase of the corrageenin-induced pleurisy.

Bronchial effects such as anti-asthmatic activity, can be demonstrated in the antigen-induced guinea pig bronchoconstriction test, e.g. as described by Anderson et al, Br. J. Pharmacol. 1983, 78, 67–74.

The trinitrobenzenesulfonic acid-induced chronic colitis test in the rat, e.g. as described by Wallace et al, Gastroenterology 1989, 96, 29–36, can be used to evaluate compounds for effects indicative of utility in inflammatory bowel diseases.

The arachidonic acid-induced mouse ear edema test, e.g. as described by Young et al, J. Invest. Dermatol. 1984, 82, 367–371 can be used to evaluate compounds for effects indicative of utility in dermatological disorders such as psoriasis.

Illustrative of the invention, the compound of example 2(d), 6-phenoxy-3-[(N-aminocarbonyl-N-hydroxy)aminomethyl]-2H-1-benzopyran, inhibits the formation of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, at an $IC_{50}$ of about 0.05 micromolar. Likewise, the compound of example 5(f) inhibits $LTB_4$ and 5-HETE formation at similar concentrations. Said compounds also cause significant inhibition of $LTB_4$ formation as determined ex vivo when administered at a dose of about 0.3 mg/kg p.o. to the dog.

Further illustrative of the invention, the compounds of example 2(d), and 5(f) at 10 mg/kg p.o. administered for two days at -1, 6, 24 and 45 hours relative to the carrageenin injection, cause inhibition of exudate volume and lower the cell count of leukocytes 48 hours after injection of carrageenin in the rat pleurisy model of inflammation. The compound of example 2(d) e.g. also inhibits colitis in the rat chronic colitis model, when administered at 100 mg/kg p.o. for 4 days.

The compounds of the invention are thus useful, particularly for the treatment and amelioration of diseases and conditions in mammals, including man, in which lipoxygenase activity or the accumulation of leukocytes (e.g. neutrophils) is involved, particularly allergic and inflammatory disorders, e.g. pulmonary allergies and inflammatory disorders (such as asthma), dermatological allergies and inflammatory disorders (such as psoriasis), also arthritic disorders (such as rheumatoid arthritis and osteoarthritis), ocular allergies and inflammatory disorders, gastrointestinal inflammatory disorders (such as inflammatory bowel diseases), as well as ischemic conditions (such as in myocardial infraction).

The compounds of the invention, depending on the structural type involved, can be prepared by the following synthetic processes:

(1) The Compounds of formula I wherein Z represents

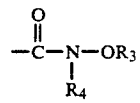

can be prepared using:

Process (a)—by condensing a carboxylic acid of formula VI

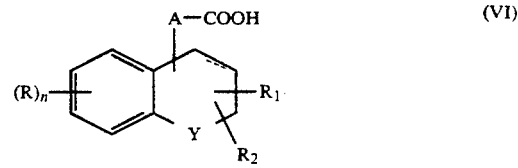

in the presence of a condensing agent, or a reactive functional derivative thereof, wherein R, $R_1$, $R_2$, A, Y and n have meaning as defined hereinabove, with a compound of the formula VII

$R_4$—NH—$OR_3$ (VII)

wherein $R_3$ and $R_4$ have meaning as defined herein, optionally in protected form when $R_3$ represents hydrogen.

The compounds of formula I wherein Z represents

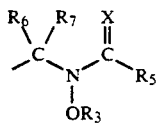

can be prepared using:

Process (b)—by condensing a compound of the formula VIII

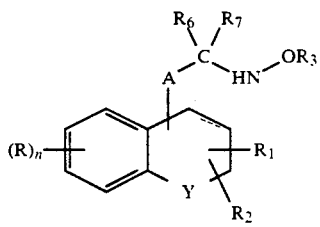

wherein R, $R_1$, $R_2$, $R_3$, $R_6$, $R_7$, A, Y and n have meaning as defined hereinabove, with a compound of the formula IX

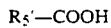

$R_5'$—COOH (IX)

in the presence of a condensing agent, or a reactive functional derivative thereof, wherein $R_5'$ represents lower alkyl, lower alkoxycarbonyl-lower alkyl, $C_3$-$C_7$-cycloalkyl, carbocyclic or heterocyclic aryl, carbocyclic or heterocyclic aryl-lower alkyl, $C_3$-$C_7$-cycloalkyl-lower alkyl, lower alkoxy or di-lower alkylamino, to obtain said compounds of formula I wherein X represents O and $R_5$ corresponds to $R_5'$; or Process (c)—by condensing a compound of the formula VIII above with phosgene or thiophosgene, followed by an amine of the formula X

$R_5''$—H (X)

wherein $R_5''$ represents amino, mono- or di-lower alkylamino, lower alkenylamino, lower alkynylamino, carbocyclic or heterocyclic arylamino, $C_3$-$C_7$-cycloalkylamino, carbocyclic or heterocyclic aryl-lower alkylamino, $C_3$-$C_7$-cycloalkyl-lower alkylamino, or lower alkoxycarbonyl-lower alkylamino, to obtain said compounds of formula I wherein $R_5$ corresponds to $R_5''$; or Process (d)—by condensing a compound of formula VIII above with an isocyanate or isothiocyanate of the formula XI

$R_8$—N═C═X (XI)

wherein X represents O or S, and $R_8$ represents a protecting group (such as tri-lower alkyl-silyl), or lower alkyl, lower alkenyl, lower alkynyl, carbocyclic or heterocyclic aryl, $C_3$-$C_7$-cycloalkyl, $C_3$-$C_7$-cycloalkyl-lower alkyl, carbocyclic or heterocyclic aryl-lower alkyl, or lower alkoxycarbonyl-lower alkyl; and, if required removing the protecting group, e.g. the tri-lower alkyl silyl group when $R_8$ represents the tri-lower alkylsilyl protecting group, to obtain said compounds of formula I wherein $R_5$ corresponds to $R_8NH$ in which $R_8$ represents hydrogen and groups as defined above.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into a free compound or into another salt; and/or a mixture of isomers or racemates obtained is separated into the single isomers or racemates; and/or, if desired, a racemate is resolved into the optical antipodes.

In starting compounds and intermediates which are converted to the compounds of the invention in a manner described herein, functional groups present, such as amino and hydroxy groups, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Synthesis", Wiley, New York, 1984.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

Also, a reactive esterified derivative of an alcohol in any of the processes cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzenesulfonic acid or 4-bromobenzenesulfonic acid. A said reactive esterified derivative is especially halo, for example chloro, bromo or iodo, or aliphatically or aromatically substituted sulfonyloxy, for example methanesulfonyloxy or 4-methylbenzenesulfonyloxy (tosyloxy).

The above processes for the synthesis of compounds of the invention can be carried out according to methodology generally known in the art for the preparation of hydroxamic acids and derivatives thereof.

The synthesis according to process (a) involving the condensation of a free carboxylic acid of formula VI with an optionally hydroxy protected hydroxylamine derivative of formula VII can be carried out in the presence of a condensing agent, e.g. diethyl phosphonocyanidate, 1,1'-carbonyldiimidazole or dicyclohexylcarbodiimide, in an inert polar solvent, such as dimethylformamide or dichloromethane.

The synthesis according to process (a) involving the condensation of a reactive functional derivative of an acid of formula VI as defined above, e.g. an acid chloride or mixed anhydride with an optionally hydroxy protected hydroxylamine derivative of formula VII, or a salt thereof, in presence of a base such as triethylamine can be carried out, at a temperature ranging preferably from about $-78°$ C. to $+75°$ C., in an inert organic solvent such as dichloromethane or toluene.

The synthesis according to process (b) involving the condensation of a carboxylic acid of formula IX or a reactive functional derivative thereof with a hydroxylamine derivative of formula VIII (optionally hydroxy protected when $R_3$ represents hydrogen) is essentially carried out as generally described for process (a).

In the case of acylation of the compounds of formula VIII wherein $R_3$ represents hydrogen, e.g. with 2 mole equivalents or excess of a functional derivative of a compound of formula IX, the N,O-bis-acylated compounds of formula III, namely those wherein $R_3$ represents $COR_5$, are obtained. The N,O-diacylated compounds of formula III, e.g. wherein $R_5$ represents lower alkyl and $R_3$ represents the corresponding $COR_5$ group, can be selectively O-deacylated under basic conditions, e.g. with aqueous lithium hydroxide to yield the corresponding compounds of formula III wherein $R_3$ represents hydrogen.

Processes c) and d) are directed to the preparation of urea derivatives, the compounds of formula I wherein Z represents group (b), i.e. of formula III wherein $R_5$ represents amino or substituted amino, from hydroxylamines of formula VIII.

The preparation according to process c) can be carried out by reacting the hydroxylamine derivative of formula VIII, preferably in hydroxy-protected form, with phosgene or thiophosgene in an inert solvent such as toluene in the presence of e.g. triethylamine, followed by condensation with the appropriate amine at a temperature of about $-25°$ C. to $+50°$ C.

The preparation according to process d) involves the condensation of a hydroxylamine of formula VIII or a salt thereof, optionally in hydroxy-protected form, with e.g. the isocyanate in an inert solvent such as toluene, acetonitrile or dioxane at a temperature ranging from room temperature to reflux temperature.

In the case of reaction of compounds of formula VIII wherein $R_3$ represents hydrogen with 2 moles of a compound of formula XI, compounds of formula III wherein $R_3$ represents $COR_5$ and $R_5$ represents $NHR_8$ are obtained.

Protected forms of hydroxylamines of formula VII and VIII (wherein $R_3$ represents hydrogen) in the above processes are those wherein the hydroxy group is protected for example as a benzyl ether or a tetrahydropyranyl ether. Removal of said protecting groups is carried out according to methods well known in the art, e.g. hydrogenolysis or acid hydrolysis, respectively.

The starting carboxylic acid of formula VI can be prepared by methods generally known in the art. For instance, the compounds of formula VI wherein Y represents oxygen, A located at the 3-position represents a direct bond, and a double bond is present between carbons at the 3- and 4-positions, can be prepared by condensing an appropriately substituted ortho-hydroxybenzaldehyde with an ester of an appropriately substituted alpha,beta-unsaturated acid, e.g. t-butyl acrylate in the presence of a base such as potassium carbonate, and hydrolyzing the resulting ester.

The corresponding carboxylic acids wherein Y represents sulfur can be similarly prepared.

In a similar manner, optionally substituted ortho-hydroxybenzaldehydes can be condensed with an appropriately substituted alpha,beta-unsaturated aldehyde or derivatives thereof, in the presence of a base such as potassium carbonate to obtain the corresponding 2H-1-benzopyran-3-carboxaldehydes which can in turn be reduced, e.g. with sodium borohydride, to the corresponding 3-hydroxymethyl-2H-1-benzopyran derivatives. Such can be converted to reactive derivatives, e.g. the corresponding 3-bromomethyl-2H-1-benzopyrans, with e.g. dibromotriphenylphosphorane, which can be in turn converted to the corresponding carboxylic acids of formula VI wherein A represents e.g. lower alkylene. Typical chain-lengthening procedures comprise conversion to the nitrile or condensation with diethyl malonate, and subsequent hydrolysis and decarboxylation as required.

Appropriately substituted 2H-1-benzopyran-3-carboxaldehydes can also be prepared as follows: by
1) converting an appropriately substituted phenol to the corresponding prepargyl ether, similarly as described in J. Org. Chemistry 38, 3832 (1973), by treating the phenol with a propargyl halide, e.g. the bromide or chloride, preferably in the presence of an alkali metal iodide, under conditions of a Williamson reaction in the presence of a base, such as potassium carbonate, in a polar inert organic solvent such as acetonitrile, to yield the corresponding substituted phenyl propargyl ether; then
2) cyclizing the phenyl propargyl ether, similarly as described in J. Org. Chem. 39, 881 (1974), to the corresponding appropriately substituted 2H-1-benzopyran at elevated temperature, e.g. at about 200°, in the presence of a high boiling tertiary amine, such as N,N-diethylaniline; and subsequently
3) treating the appropriately substituted 2H-1-benzopyran with a Vilsmeier-Haack formylation reagent, consisting of a tertiary formamide and e.g. phosphorus oxychloride, preferably N-formylpiperidine or N-formylmorpholine and phosphorus oxychloride, in an inert organic solvent, such as methylene chloride, to obtain the corresponding substituted 2H-1-benzopyran-3-carboxaldehyde.

The unsaturated starting materials of formula VI (the 2H-1-benzopyrans) can be converted to the corresponding saturated compounds (the 3,4-dihydrobenzopyrans) e.g. by catalytic hydrogenation under conditions well-known in the art. As to other starting materials of formula VI, for example 3,4-dihydro-2H-1-benzothiopyran-3-carboxylic acids can be prepared e.g. as described in U.S. Pat. No. 4,801,605 or Synthesis 1976, 409–411, 3,4-dihydro-2H-1-benzopyran-2-carboxylic acid can be prepared as described in Eur. J. Med. Chem. 22 (1987), 539–544, and 3,4-dihydro-2H-1-(benzopyran or benzothiopyran)-4-carboxylic acids can be prepared according to U.S. Pat. No. 4,305,955.

The starting materials of formula VI wherein Y represents S can be converted to the sulfoxide or sulfone thereof by treatment with e.g. a peracid, preferably m-chloroperbenzoic acid, to obtain either the sulfoxide or sulfone depending on the quantity of peracid used. The sulfoxides may also be prepared by treatment with a salt of periodic acid, e.g. sodium periodate.

The hydroxylamine derivatives of formula VII are known or are prepared according to methods well-known in the art for the preparation of hydroxylamines e.g. by condensing corresponding halides with e.g. benzyl or tetrahydropyranyl O-protected hydroxylamine or by reduction of oximes.

The starting hydroxylamines of formula VIII may be prepared from a corresponding reactive derivative of an alcohol of formula XII

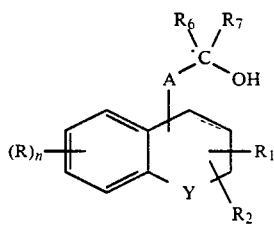

wherein R, $R_1$, $R_2$, $R_6$, $R_7$, Y, A and n have meaning as defined hereinabove, such as the corresponding bromide, tosylate or mesylate derivative, by condensing such with e.g. O-benzylhydroxylamine, O-tetrahydropyranylhydroxylamine or O-(2-methoxy-2-propyl)-hydroxylamine.

Alternatively hydroxylamines of formula VIII wherein at least one of $R_6$ and $R_7$ represents hydrogen can be prepared from the corresponding aldehyde or ketone by conversion to the oxime with e.g. hydroxylamine hydrochloride according to known methods, followed by reduction to the hydroxylamine with e.g. borane-pyridine complex or sodium cyanoborohydride in acidic medium.

The alcohols of formula XII and corresponding aldehydes or ketones may be prepared e.g. from the corresponding acids of formula VI or ester derivatives thereof according to methods well-known in the art. For example, such can be reduced to the alcohol wherein $R_6$ and $R_7$ represent hydrogen using an appropriate reducing agent such as lithium aluminum hydride or aluminum hydride. The aldehydes or alcohols, for instance the 3-substituted 2H-1-benzopyran derivatives can also be prepared as described hereinabove, starting with o-hydroxybenzaldehydes or a phenyl propargyl ethers.

The carboxylic acids of formula IX and reactive derivatives thereof are known in the art or can be prepared according to methods well-known in the art; similarly the amines of formula X, and the isocyanates and isothiocyanates of formula XI; also alcohols of formula XII can be prepared from acids of formula VI.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

Compounds of the invention and intermediates can also be converted into each other according to methods generally known per se, and illustrated herein, e.g. by hydrogenation of a double bond. For example, 2H-1-benzopyrans of the invention are hydrogenated to the corresponding 3,4-dihydrobenzopyrans using e.g. palladium on charcoal as catalyst. Also, carboxamides, e.g. N-acyloxycarboxamides, of the invention can be converted to the corresponding thioamides by reaction with e.g. Lawesson's reagent.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids (wherein $R_3$ represents hydrogen) can thus be resolved into their optical antipodes e.g. by fractional crystallization of d- or l-(alphamethylbenzylamine, cinchonidine, cinchonine, quinine, quinidine, ephedrine, dehydroabietylamine, brucine or strychnine)-salts.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

In view of the close relationship between the free compounds and the compounds in the form of their salts, whenever a compound is referred to in this context, a correponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit lipoxygenase, in particular 5-lipoxygenase, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application.

Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or efferverscent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The pharmaceutical formulations contain an effective lipoxygenase inhibiting amount of a compound of the invention as defined above either alone, or in combination with another therapeutic agent selected from e.g. an anti-inflammatory agent with cyclooxygenase inhibiting activity, a leukotriene receptor antagonist, a thromboxane synthetase inhibitor, a thromboxane receptor antagonist, an antihistamine, a platelet activating factor (PAF) antagonist or a serotonin receptor antagonist, each at an effective therapeutic dose as reported in the art. Such therapeutic agents are well-known in the art.

Examples of anti-inflammatory agents with cyclooxygenase inhibiting activity are diclofenac, naproxen, ibuprofen, and the like.

Examples of leukotriene antagonists are LY-223982, SC-41930, ICI-204219, L-660711, and the like.

Examples of thromboxane synthetase inhibitors are ozagrel (OKY-046), pirmagrel (CGS 13080), CGS 12970, CGS 15435 and the like.

Examples of thromboxane receptor antagonists are sulotroban, ICI-192605, GR-32191, SQ-30741, L-655240 and the like.

Examples of antihistaminic agents are astemizole, loratidine, terfanidine, chlorpheniramine and the like.

Examples of platelet activating factor antagonists are BN-52063, WEB-2086, CV-3988, RP-48740, L-652731 and the like.

Examples of serotonin antagonists are ketanserin, cinanserin, irindalone and the like.

In conjunction with another active ingredient, a compound of the invention may be administered either simultaneously, before or after the other active ingredient, either separately by the same or different route of administration or together in the same pharmaceutical formulation.

The invention further particularly relates to a method of inhibiting 5-lipoxygenase activity in mammals including man, and of treating diseases and conditions responsive thereto, particularly inflammatory and allergic disorders, which comprises administering to a mammal in need thereof an effective amount of a compound of the invention or of a pharmaceutical composition comprising a said compound in combination with one or more pharmaceutically acceptable carriers.

Excessive lipoxygenase activity has been implicated in various diseases and abnormal metabolic conditions including:

a) allergic conditions such as hay fever (allergic rhinitis), extrinsic asthma, skin allergies, allergic bowel diseases (incl. coeliac disease), allergic eye conditions such as allergic conjuctivitis;

b) inflammatory conditions such as inflammatory bowel diseases, irritable bowel syndrome, mucous colitis, ulcerative colitis, Crohn's disease, gastritis, esophagitis, hepatitis;

c) cardiovascular conditions such as myocardial ischemia, cerebral ischemia, atherosclerosis, angina, and renal ischemia;

d) pulmonary conditions such as intrinsic asthma, bronchitis, cystic fibrosis;

e) arthritic conditions such as rheumatoid arthritis, rheumatoid spondylitis, gouty arthritis, osteoarthritis and the like;

f) cutaneous disorders such as psoriasis, eczema and dermatitis;

g) multiple sclerosis, arteriosclerosis of various etiology and shock such as endotoxin shock. and h) tumor metastasis.

Conditions or syndromes responsive to the inhibition of lipoxygenase are those cited above, e.g. rheumatic diseases such as rheumatoid arthritis, allergic disorders, asthma and psoriasis.

The dosage of active compound administered is dependent on the species of warm-blooded animal (mammal), the body weight, age and individual condition, and on the form of administration. A unit dosage for oral administration to a mammal of about 50 to 70 kg may contain between about 20 and 250 mg of the active ingredient.

The following examples are intended to illustrate the invention and are not to be construed as being limitations thereon. Temperatures are given in degrees Centrigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1 a) 6-Benzyloxy-2H-1-benzopyran-3-carboxylic acid (362 mg, 1.33 mmol) and DMF (97 mg, 1.33 mmol) are dissolved in 5 ml of dichloromethane. To this is added oxalyl chloride (0.38 g, 2.99 mmol) and the mixture is stirred until no further gas evolution is observed (2 hours). This acid chloride solution is slowly added to a mixture of N-methylhydroxylamine hydrochloride (0.44 g, 5.32 mmol) and triethylamine (0.81 g, 7.98 mmol) in THF/water (4.1 ml/0.99 ml). The resultant mixture is stirred at room temperature for 1 hour, and poured onto 100 ml of 2N aqueous HCl. The mixture is extracted twice with dichloromethane and the organic phase is dried (MgSO$_4$). Evaporation followed by trituration of the residual solid with ethyl acetate/hexane gives 6-benzyloxy-N-hydroxy-N-methyl-2H-1-benzopyran-3-carboxamide, m.p. 143°-146° C., as a pale yellow solid.

The starting material is prepared as follows: 4-Benzyloxyphenol (20 g, 0.1 mol) is dissolved in 24 ml of ethanol and 120 ml of 20% aqueous sodium hydroxide (24 g NaOH, 0.6 mol), and heated at 70° C. To this is added chloroform (23.9 g, 0.2 mol) dropwise and the mixture is stirred for 3.5 hours at 70° C. The mixture is cooled and evaporated. The residue is then treated with conc. HCl until the pH of the solution is 1 to 3. The mixture is extracted with ether three times, and the combined organic layer is dried (MgSO$_4$), evaporated and purified by silica gel chromatography (5% ethyl acetate/hexane) to give 5-benzyloxy-2-hydroxybenzaldehyde as a pale yellow, crystalline solid, m.p. 94°-96° C.

5-Benzyloxy-2-hydroxybenzaldehyde (2.01 g, 8.80 mmol) is dissolved in 30 ml of DMF and treated successively with potassium carbonate (1.22 g, 8.80 mmol) and tert-butyl acrylate (1.22 g, 13.2 mmol). The mixture is heated at 100° C. for 1 hour. The temperature is gradually raised to 135° C. over a period of 2 hours, and held at 135° C. for 1 hour. The resultant dark mixture is cooled and evaporated to remove most of DMF. The residue is partitioned between ether and water, and the aqueous phase is discarded. The organic layer is dried (MgSO$_4$), evaporated and purified by silica gel chromatography (6% ethyl acetate/hexane) to give tert-butyl 6-benzyloxy-2H-1-benzopyran-3-carboxylate as a yellow crystalline solid, m.p. 64°-67° C.

The tert-butyl ester (1.1 g, 3.25 mmol) is dissolved in 10 ml of trifluoroacetic acid and the mixture is stirred at room temperature overnight. This is poured into 50 ml of water and the precipitate is collected by filtration. The solid is washed with water several times and dried in vacuo. Crystallization from ethyl acetate/hexane yield 6-benzyloxy-2H-1-benzopyran-3-carboxylic acid as a yellow solid, m.p. 184°-189° C.

b) Similarly prepared is N-hydroxy-N-methyl-7-methoxy-2H-1-benzopyran-3-carboxamide, m.p. 115°-117° C., starting from 4-methoxy-2-hydroxybenzaldehyde.

c) Similarly prepared is N-hydroxy-N-methyl-2H-1-benzopyran-3-carboxamide, m.p. 70°-73° C., starting from salicylaldehyde.

d) Similarly prepared is N-hydroxy-N-methyl-6-phenoxy-2H-1-benzopyran-3-carboxamide, starting from 5-phenoxy-2-hydroxybenzaldehyde (5-phenoxysalicylaldehyde).

EXAMPLE 2 a) 3-[(N-hydroxyamino)methyl]-6-methoxy-2H-1-benzopyran hydrochloride (480 mg, 1.97 mmol) is suspended in ether and treated with 2N aqueous sodium hydroxide. The ether layer is removed and the aqueous phase is extracted three times with ether. The combined organic phases are dried over magnesium sulfate and evaporated to give the free hydroxylamine derivative as a pale yellow solid. This amine and trimethylsilyl isocyanate (322 mg, 2.79 mmol) are dissolved in 15 ml of 1,4-dioxane and the mixture is heated at reflux for 30 minutes. The mixture is cooled to 5° C., and treated with aqueous saturated ammonium chloride solution. Two extractions with ethyl acetate are carried out and the combined organic layer is dried (MgSO$_4$). Evaporation followed by crystallization from ethyl acetate/hexane gives the urea 3-[(N-aminocarbonyl-N-hydroxy)aminomethyl]-6-methoxy-2H-1-benzopyran, m.p. 165°-167° C., the compound of formula V wherein R is 6-methoxy, $R_1$ and $R_6$ are hydrogen and $R_5$ is $NH_2$.

The starting material is prepared as follows: 5-Methoxy-2-hydroxybenzaldehyde (25 g, 0.16 mol) and potassium carbonate (22.7 g, 0.16 mol) are taken up in 300 ml of 1,4-dioxane and treated with acrolein (13.8 g, 0.25 mol). The mixture is heated at 100° C. for 1 hour, and allowed to cool. The mixture is diluted with water and extracted three times with ether. The combined ether extracts are dried (MgSO$_4$) and evaporated. The residual oil is dissolved in a minimal amount of ethyl acetate (approx. 40 ml) and passed through 40 g of silica gel. The gel is successively washed with several portions of a hexane/ether mixture (3:1) until no further fluorescent material is eluted. The organic phase is evaporated and the residue is crystallized from ethyl acetate/hexane to give 6-methoxy-2H-1-benzopyran-3-carboxaldehyde as a yellow solid, m.p. 49°-50° C.

The above carboxaldehyde (8.5 g, 44.7 mmol) is suspended in 100 ml of absolute ethanol and treated with sodium borohydride (0.68 g, 44.7 mmol). After 15 minutes, the resultant mixture is evaporated, partitioned between ether and water, and quenched by addition of 2N aqueous HCl. Ether is removed and the aqueous phase is extracted twice with ether. The combined organic phases are dried (MgSO$_4$) and evaporated. Purification of the residual oil by silica gel chromatography (15% ethyl acetate/hexane) gives 6-methoxy-3-(hydroxymethyl)-2H-1-benzopyran as a yellow oil which partially solidifies while stored in a refrigerator.

6-Methoxy-3-(hydroxymethyl)-2H-1-benzopyran (4.35 g, 22.6 mmol) is dissolved in 70 ml of dry acetonitrile and treated with dibromotriphenylphosphorane (9.56 g, 22.6 mmol). After 15 min, the mixture is evaporated in vacuo. The residue is triturated with 100 ml of an ether/hexane mixture (1:1). The solid is removed by filtration (medium frit) and washed with several 50 ml portions of the ether/hexane mixture. The organic extracts are combined and evaporated to give 6-methoxy-3-(bromomethyl)-2H-1-benzopyran which is used without any further purification.

A solution of the above bromide (2.32 g, 9.09 mmol) in 10 ml of DMF is added to a stirred solution of O-(2-methoxy-2-propyl)hydroxylamine (2.87 g, 27.28 mmol) and triethylamine (1.01 g, 10.0 mmol) in 30 ml of DMF. The reaction is allowed to proceed overnight. The reaction mixture is diluted with water and extracted three times with ether. The combined ether phases are dried (MgSO$_4$) and evaporated. The residue is purified by silica gel chromatography (15% ethyl acetate/hexane) to give 3-[N-(2-methoxy-2-propyloxy)-aminomethyl]-6-methoxy-2H-1-benzopyran as a yellow oil.

The above protected hydroxylamine (1.68 g, 6.01 mmol) is dissolved in 15 ml of methanol and treated with 2.5 ml of conc. HCl. The mixture is stirred for 1 hour and evaporated in vacuo. The residual solid is triturated with an ether/hexane mixture (1:1), and collected by filtration. Drying of the crystalline solid under high vacuum affords 3-(N-hydroxyaminomethyl)-6-methoxy-2H-1-benzopyran hydrochloride.

Similarly prepared are:

b) 6-benzyloxy-3-[(N-aminocarbonyl-N-hydroxy)aminomethyl]-2H-1-benzopyran, m.p. 159°–161° C.

The starting material is prepared as follows: 2,5-Dihydroxybenzaldehyde (25.0 g, 0.18 mol) is dissolved in 375 ml of 1,4-dioxane. To this is sequentially added potassium carbonate (50.0 g, 0.36 mol) and acrolein (15.22 g, 0.27 mol). The mixture is heated at reflux overnight, cooled, and partitioned between water and ether. The aqueous layer is removed and extracted twice with ether. The combined organic layers are dried (MgSO$_4$) and evaporated. Trituration of the residue with dichloromethane, followed by filtration and drying, yields 6-hydroxy-2H-1-benzopyran-3-carboxaldehyde, m.p. 163°–165° C., as a yellow crystalline solid.

A mixture of 6-hydroxy-2H-1-benzopyran-3-carboxaldehyde (25.0 g, 0.14 mol) and potassium carbonate (39.2 g, 0.28 mol) in 500 ml of DMF is treated with benzyl bromide (26.7 g, 0.16 mol). The mixture is stirred overnight at room temperature. Water is added and three extractions with dichloromethane are carried out. The extract is dried (MgSO$_4$) and evaporated to dryness. The residue is crystallized from hot ethyl acetate to give 6-benzyloxy-2H-1-benzopyran-3-carboxaldehyde, m.p. 112°–114° C.

The above aldehyde is converted to 3-(N-hydroxyaminomethyl)-6-benzyloxy-2H-1-benzopyran as described under (a).

c) 6-(4-Trifluoromethylbenzyloxy)-3-[(N-aminocarbonyl-N-hydroxy)aminomethyl]-2H-1-benzopyran, m.p. 160°–162° C.

The starting material is prepared as follows: A mixture of 6-hydroxy-2H-1-benzopyran-3-carboxaldehyde (2.50 g, 14.2 mmol) and potassium carbonate (3.62 g, 38.4 mmol) in 50 ml of DMF is treated with 4-trifluoromethylbenzyl bromide (3.73 g, 15.6 mmol). The reaction is allowed to proceed overnight at room temperature. The mixture is diluted with water and extracted three times with dichloromethane. The combined organic layers are washed once with water, dried (MgSO$_4$), and evaporated. Purification by silica gel chromatography (20% ethyl acetate/hexane) yields 6-(4-trifluoromethylbenzyloxy)-2H-1-benzopyran-3-carboxaldehyde, m.p. 108°–110° C.

The above aldehyde is converted to 3-(N-hydroxyaminomethyl)-6-(4-trifluoromethylbenzyloxy)-2H-1-benzopyran as described under (a).

d) 3-[(N-Aminocarbonyl-N-hydroxy)aminomethyl]-6-phenoxy-2H-1-benzopyran, m.p. 168°–170° C., the compound of formula V wherein R is 6-phenoxy, $R_1$ and $R_6$ are hydrogen and $R_5$ is NH$_2$.

The starting material is prepared as follows: 4-Phenoxyphenol (20.0 g, 107 mmol) and sodium hydroxide (3.8 g, 845 mmol) are dissolved in a water/ethanol (130 ml/26 ml) mixture and heated at 70° C. To this reaction mixture is added chloroform (24.6 g, 215 mmol) dropwise over 45 minutes, and heating is continued for 3 hours. The mixture is cooled to room temperature, and then evaporated. The aqueous phase is acidified with conc. HCl to pH 1–3, and extracted twice with ether. The extracts are dried (MgSO$_4$) and evaporated. Silica gel chromatography (10% ethyl acetate/hexane) of the residual oil yields 5-phenoxy-2-hydroxybenzaldehyde as a yellow solid, m.p. 54°–55° C., which is converted to 3-(N-hydroxyaminomethyl)-6-phenoxy-2H-1-benzopyran as described under (a).

e) 3-[(N-Aminocarbonyl-N-hydroxy)aminomethyl]-6-(n-hexyloxy)-2H-1-benzopyran, m.p. 147°–148° C.

The starting material is prepared as follows: A mixture of 6-hydroxy-2H-1-benzopyran-3-carboxaldehyde (4.0 g, 22.7 mmol) and potassium carbonate (6.26 g, 45.3 mmol) in 80 ml of DMF is treated with n-hexyl bromide (4.5 g, 27.2 mmol). The mixture is stirred overnight at room temperature. Additional potassium carbonate (3.1 g, 22.4 mmol) and n-hexyl bromide (1.0 g, 6.1 mmol) are added and, after another overnight reaction, no more starting material is detected in the reaction mixture. The reaction mixture is diluted with water and extracted three times with dichloromethane. The combined organic phases are dried (MgSO$_4$) and evaporated. Purification by silica gel chromatography (10% ethyl acetate/hexane) yields 6-(n-hexyloxy)-2H-1-benzopyran-3-carboxaldehyde, m.p. 36°–38° C., which is converted as described above to 3-(N-hydroxyaminomethyl)-6-(n-hexyloxy)-2H-1-benzopyran.

f) 3-[(N-Aminocarbonyl-N-hydroxy)aminomethyl]-6-(3-phenylpropyloxy)-2H-1-benzopyran, m.p. 145°–147° C.

The starting material is prepared as follows: A solution of 6-hydroxy-2H-1-benzopyran-3-carboxaldehyde (5.0 g, 28.4 mmol) in 100 ml of DMF is treated with potassium carbonate (7.85 g, 56.8 mmol) and 1-bromo-3-phenylpropane (6.22 g, 31.2 mmol). The reaction mixture is stirred for 2 days at room temperature. This is partitioned between water and dichloromethane and the aqueous layer is extracted twice with dichloromethane. The combined organic layer is dried (MgSO$_4$), and evaporated. The residue is chromatographed (silica gel, 20% ethyl acetate/hexane) to afford 6-(3-phenylpropyloxy)-2H-1-benzopyran-3-carboxaldehyde, m.p. 71°–73° C., as an oil which crystallizes on standing. The aldehyde is converted to 3-(N-hydroxyaminomethyl)-6-(3-phenylpropyloxy)-2H-1-benzopyran as described above.

g) 3-[(N-Aminocarbonyl-N-hydroxy)aminomethyl]-6-benzyloxy-2-methyl-2H-1-benzopyran, m.p. 132°–136° C.

The starting material is prepared as follows: A mixture of 2,5-dihydroxybenzaldehyde (5.0 g, 36.2 mmol), crotonaldehyde (3.8 g, 54.3 mmol), and potassium carbonate (10.0 g, 72.4 mmol) in 75 ml of 1,4-dioxane is heated at reflux for 6 hours. The mixture is cooled and poured into water. This is extracted (3×) with dichloromethane, and the combined organic layers are dried (MgSO$_4$) and concentrated to dryness to give 6-hydroxy-2-methyl-2H-1-benzopyran-3-carboxaldehyde as a colored solid. Such is converted to 6-benzyloxy-2- methyl-2H-1-benzopyran-3-carboxaldehyde, m.p. 107°–109° C., which is in turn converted to 3-(N-hydroxyaminomethyl)-6-benzyloxy-2-methyl-2H-1-benzopyran as described above.

h) 3-[(N-Aminocarbonyl-N-hydroxy)aminomethyl]-6-phenoxy-2-methyl-2H-1-benzopyran, m.p. 122°–124° C.

The starting material is prepared as follows: A mixture of 5-phenoxysalicylaldehyde (6.52 g, 30.4 mmol), crotonaldehyde (3.2 g, 45.7 mmol) and potassium carbonate (8.41 g, 60.9 mmol) in 100 ml of 1,4-dioxane is heated at reflux for 2 hours. The mixture is cooled, diluted with water, and extracted three times with dichloromethane. The combined organic layers are dried (MgSO$_4$) and evaporated. Purification by flash chromatography (silica gel, 7% ethyl acetate/hexane) yields 6-phenoxy-2-methyl-2H-1-benzopyran-3-carboxaldehyde which is converted to 6-phenoxy-2-methyl-3-(N-hydroxyaminomethyl)-2H-1-benzopyran as described above.

i) 3-[(N-Aminocarbonyl-N-hydroxy)aminomethyl]-6-phenoxy-2,2-dimethyl-2H-1-benzopyran, m.p. 124°–127° C., starting from 3-methylcrotonaldehyde as described under h).

j) 3-[(N-Aminocarbonyl-N-hydroxy)aminomethyl]-6-phenoxy-2-phenyl-2H-1-benzopyran, m.p. 158°–161° C.

The starting material is prepared as follows: A mixture of 5-phenoxysalicylaldehyde (5.00 g, 23.3 mmol), cinnamylaldehyde (3.39 g, 25.7 mmol) and potassium carbonate (6.45 g, 46.7 mmol) in 70 ml of 1,4-dioxane is heated at reflux overnight. The mixture is cooled, diluted with water, and extracted three times with dichloromethane. The combined organic layers are dried (MgSO$_4$) and evaporated. Purification by flash chromatography (silica gel, 5% ethyl acetate(EtOAc)/hexane) yields 6-phenoxy-2-phenyl-2H-1-benzopyran-3-carboxaldehyde.

k) 3-[(N-Aminocarbonyl-N-hydroxy)aminomethyl]-6-(p-n-butylphenoxy)-2H-1-benzopyran.

l) 3-[(N-Aminocarbonyl-N-hydroxy)aminomethyl]-6-(3-pyridylmethyloxy)-2H-1-benzopyran.

m) 3-[(N-Aminocarbonyl-N-hydroxy)aminomethyl]-6-bromo-2H-1-benzopyran.

The starting material is prepared as follows: A mixture of 5-bromosalicylaldehyde (10.3 g, 51.1 mmol) and potassium carbonate (7.0 g, 51.1 mmol) in 30 ml of 1,4-dioxane is treated with acrolein (4.3 g, 76.6 mmol). The mixture is heated at reflux for 2 hours and allowed to cool. This is partitioned between ether and water, and separated. The aqueous layer is extracted once with ether, and the organic phases are combined, dried (MgSO$_4$) and evaporated. Flash chromatography (silica gel, 8% ethyl acetate/hexane) yields 6-bromo-2H-1-benzopyran-3-carboxaldehyde, m.p. 103°–104° C., which is converted to the final product as described above.

n) 3-[(N-Aminocarbonyl-N-hydroxy)aminomethyl]-6-phenyl-2H-1-benzopyran, m.p. 148°–153° C.

The starting material is prepared as follows: 6-Bromo-2H-1-benzopyran-3-carboxaldehyde (5.00 g, 20.9 mmol), phenylboronic acid (2.81 g, 23.1 mmol), and tetrakis(triphenylphosphine)palladium(0) (725 mg, 0.63 mmol) are dissolved in 50 ml of toluene and treated with 25 ml of aqueous 2M sodium carbonate under nitrogen. The mixture is heated at reflux for 6 hours. The reaction mixture is cooled and extracted with ether (3×). The combined ethereal extracts are dried (MgSO$_4$) and evaporated. Flash chromatography (silica gel, 5% ethyl acetate/hexane), yields 6-phenyl-2H-1-benzopyran-3-carboxaldehyde, m.p. 108°–110° C., which is converted to the final product as described above.

o) 3-[(N-Aminocarbonyl-N-hydroxy)aminomethyl]-6-(cyclohexylmethyloxy)-2H-1-benzopyran, m.p. 129°–135° C. The starting material is prepared by condensation of 6-hydroxy-2H-1-benzopyran-3-carboxaldehyde with cyclohexylmethyl bromide.

p) 3-[(N-Aminocarbonyl-N-hydroxy)aminomethyl]-6-(p-tert-butylphenoxy)-2H-1-benzopyran, m.p. 137°–140° C.

The starting material is prepared as follows: 4-Bromoanisole (28.06 g, 0.15 mol), 4-tert-butylphenol (27.04 g, 0.18 mol), potassium carbonate (6.9 g, 0.05 mol) and copper powder (0.2 g, 3 mmol) are combined under nitrogen and heated at 210° C. for 2.5 hours. The mixture is then cooled and treated with 1N NaOH to pH 12. Three extractions with ether are carried out. The combined extracts are dried (MgSO$_4$) and evaporated. The residue is distilled under vacuum to yield 4-(p-tert-butylphenoxy)anisole, b.p. 220° C./20 mmHg. A mixture of the product (18.55 g, 68.5 mmol) and pyridinium hydrochloride (500 g, 4.33 mol) is heated at 230° C. for 2 hours under nitrogen, then cooled to room temperature and partitioned between water and ether. The aqueous layer is extracted with ether, the extract is dried (MgSO$_4$) and evaporated to give 4-(p-tert-butylphenoxy)phenol as an oil. Such is converted to 5-(p-tert-butylphenoxy)salicylaldehyde, which is then converted to 3-(N-hydroxyaminomethyl)-6-(p-tert-butylphenoxy-2H-1-benzopyran as described hereinabove.

q) 3-[(N-Aminocarbonyl-N-hydroxy)aminomethyl]-6-n-heptyl-2H-1-benzopyran, m.p. 147°–150° C. which is prepared starting from 4-n-heptylphenol as described hereinabove.

r) 3-[(N-Aminocarbonyl-N-hydroxy)aminomethyl]-6-(p-fluorophenoxy)-2H-1-benzopyran, m.p. 179°–180° C.

s) 3-[(N-Aminocarbonyl-N-hydroxy)aminomethyl]-6-phenoxy-2-n-propyl-2H-1-benzopyran, as an oil, starting from trans-2-hexenal and 5-phenoxysalicylaldehyde.

t) 3-[1'-(N-Aminocarbonyl-N-hydroxyamino)ethyl]-6-phenoxy-2H-1-benzopyran, m.p. 169°–171° C. (crystallized from acetonitrile).

The starting material is prepared as follows: 5-Phenoxysalicylaldehyde (6.17 g, 28.8 mmol) is dissolved in 100 ml of 1,4-dioxane and treated with potassium carbonate (7.96 g, 57.6 mmol) and methyl vinyl ketone (3.03 g, 43.2 mmol) under nitrogen. The mixture is heated at reflux for 3 hours. Water is added and three extractions with dichloromethane are carried out. The organic extracts are combined, dried (MgSO$_4$) and evaporated. Purification by flash chromatography (silica gel, 15% EtOAc/hexane) yields 3-acetyl-6-phenoxy-2H-1-benzopyran as a solid.

The ketone (2.53 g, 9.5 mmol) is dissolved in 90 ml of an EtOH/pyridine mixture (1:1), and treated with hydroxylamine hydrochloride (0.99 g, 14.3 mmol). The mixture is stirred for 2 days. The reaction mixture is partitioned between ether and water, and the aqueous layer is extracted twice with ether. The combined organic layer is then washed twice with 2N HCl and water, dried (MgSO$_4$), and evaporated. The residue is purified by flash chromatography (10% EtOAc/hexane) to give 3-acetyl-6-phenoxy-2H-1-benzopyran oxime as a crystalline solid.

The oxime (1.06 g, 3.77 mmol) is dissolved in 7.0 ml of trifluoroacetic acid and 7.0 ml of dichloromethane and cooled to 0° C. To this is added borane-pyridine complex (7.0 g, 75.4 mmol) in 10 ml of dichloromethane at 0° C. After the addition, the mixture is heated at 40° C. for 3 hours. The mixture is allowed to cool, and treated with conc. HCl (15 ml). The mixture is again heated to 40° C. for 1 hour. This mixture is cooled to 0° C. and brought to pH 10 by addition of ammonium hydroxide. Three extractions with ether are carried out. The combined ether layer is dried (MgSO$_4$) and evaporated to give crude 3-(1'-hydroxyamino)-ethyl-6-phenoxy-2H-1-benzopyran, which is used directly for condensation with trimethylsilyl isocyanate.

EXAMPLE 3

A mixture of 6-methoxy-3-(bromomethyl)-2H-1-benzopyran (552 mg, 2.16 mmol) and potassium carbonate (597 mg, 4.32 mmol) in 10 ml of DMF is treated with O-acetyl-N-tert-butoxycarbonylhydroxylamine (378 mg, 2.16 mmol) at room temperature. The mixture is stirred for 3 h, diluted with ether, washed once with water, dried (MgSO$_4$) and evaporated. Purification of the residual oil by silica gel chromatography (10% ethyl acetate/hexane) yields 3-[(N-acetoxy-N-tert-butoxycarbonyl)aminomethyl-]-6-methoxy-2H-1-benzopyran as a colorless solid.

The starting material is prepared as follows: tert-Butyl N-hydroxycarbamate (3.89 g, 29.2 mmol) is dissolved in 25 ml of dichloromethane and cooled to 0° C. To this is added triethylamine (3.25 g, 32.1 mmol) and acetyl chloride (2.29 g, 29.2 mmol) dropwise. The mixture is extracted with ether and the extracts are washed with aqueous 2N HCl, water, 10% sodium bicarbonate, water, dried (MgSO$_4$) and evaporated. The resulting colorless oil is purified by silica gel chromatography (10% ethyl acetate/hexane) to give O-acetyl-N-tert-butoxycarbonylhydroxylamine as a colorless oil.

EXAMPLE 4

3-[(N-acetoxy-N-tert-butoxycarbonyl)aminomethyl]-6-methoxy-2H-1-benzopyran (261 mg, 0.75 mmol) is added to a mixture of lithium hydroxide (monohydrate, 315 mg, 7.5 mmol) in isopropanol-water-dioxane (30 ml, 1:1:1). The mixture is stirred for 10 minutes at room temperature, and covered with ether. The mixture is then acidified with 6N aqueous HCl to pH of approx. 3, and the aqueous phase is removed. The ether layer is then dried (MgSO$_4$) and evaporated. Crystallization from ethyl acetate/hexane gives 3-[(N-tert-butoxycarbonyl-N-hydroxy)aminomethyl]-6-methoxy-2H-1-benzopyran, m.p. 79°–80° C.

EXAMPLE 5 a) 3-(N-hydroxyaminomethyl)-6-phenoxy-2H-1-benzopyran (1.56 g, 5.79 mmol) is dissolved in 40 ml of 1,4-dioxane and treated with phenyl isocyanate (0.98 g, 8.23 mmol). The mixture is heated at reflux for 30 minutes and allowed to cool. Aqueous ammonium chloride is added and the mixture is extracted with ethyl acetate (2×). The combined organic layers are dried (MgSO$_4$) and evaporated. Crystallization from THF/hexane yields 3-[(N-hydroxy-N-(N'-phenyl)aminocarbonyl)aminomethyl]-6-phenoxy-2H-1-benzopyran, m.p. 168°–171° C.

b) Similarly prepared is 3-[(N-hydroxy-N-(N'-methyl)aminocarbonyl)aminomethyl]-6-phenoxy-2H-1-benzopyran, m.p. 157°–161° C.

c) Similarly prepared is 3-[(N-hydroxy-N-(N'-benzyl)aminocarbonyl)aminomethyl]-6-phenoxy-2H-1-benzopyran, m.p. 135°–140° C.

d) Similarly prepared is 3-[{N-(N'-ethylaminocarbonyl)-N-hydroxy}aminomethyl]-6-phenoxy-2H-1-benzopyran, m.p. 155°–157° C., the compound of formula V wherein R=6-phenoxy, R$_1$ and R$_6$=hydrogen and R$_5$=ethylamino.

e) Similarly prepared is 3-[{N-(N'-(ethoxycarbonylmethyl)aminocarbonyl)-N-hydroxy}-aminomethyl]-6-phenoxy-2H-1-benzopyran, m.p. 136°–138° C., the compound of formula V wherein R=6-phenoxy, R$_1$ and R$_6$=hydrogen and R$_5$=(ethoxycarbonylmethyl)amino.

f) Similarly prepared is 3-[{N-(N'-methylaminocarbonyl)-N-hydroxy}aminomethyl]-6-(p-fluorophenoxy)-2H-1-benzopyran, m.p. 171°–172° C., the compound of formula V wherein R=6-(p-fluorophenoxy), R$_1$ and R$_6$=hydrogen and R$_5$=methylamino.

g) Similarly prepared is 3-[{N-(N'-propylaminocarbonyl)-N-hydroxy}aminomethyl]-6-phenoxy-2H-1-benzopyran, m.p. 134°–137° C., the compound of formula V wherein R=6-phenoxy, R$_1$ and R$_6$=hydrogen and R$_5$=n-propylamino.

h) 3-[{N-(N'-Isopropylaminocarbonyl)-N-hydroxy}aminomethyl]-6-phenoxy-2H-1-benzopyran, m.p. 129°–130° C., the compound of formula V wherein R=6-phenoxy, R$_1$ and R$_6$=hydrogen and R$_5$=isopropylamino.

i) 3-[{N-(N'-tert-Butylaminocarbonyl)-N-hydroxy}aminomethyl]-6-phenoxy-2H-1-benzopyran, m.p. 148°–150° C., the compound of formula V wherein R=6-phenoxy, R$_1$ and R$_6$=hydrogen and R$_5$=tert-butylamino.

j) 3-[{N-(N'-Butylaminocarbonyl)-N-hydrox-y}aminomethyl]-6-phenoxy-2H-1-benzopyran, m.p. 135°–136° C., the compound of formula V wherein R=6-phenoxy, R$_1$ and R$_6$=hydrogen and R$_5$=n-butylamino.

k) 3-[{N-(N'-Allylaminocarbonyl)-N-hydroxy}aminomethyl]-6-phenoxy-2H-1-benzopyran, m.p. 127°–132° C., the compound of formula V wherein R=6-phenoxy, R$_1$ and R$_6$=hydrogen and R$_5$=allylamino.

EXAMPLE 6

A solution of 3-(N-hydroxyaminomethyl)-6-phenoxy-2H-1-benzopyran (0.67 g, 2.48 mmol) and pyridine (0.49 g, 6.19 mmol) in 30 ml of THF is cooled to 0° C. Acetyl chloride (0.49 g, 6.19 mmol) is slowly added and the mixture is stirred for 45 minutes at 0° C. The mixture is then diluted with ethyl acetate and washed with aqueous 2N HCl, dried (MgSO$_4$) and evaporated to give 3-[(N-acetyloxy-N-acetyl)aminomethyl]-6-phenoxy-2H-1-benzopyran, m.p. 153°–157° C.

This is dissolved in 40 ml of an isopropanol/water mixture (1:1) and treated with 0.94 g (25 mmol) of LiOH monohydrate for 20 minutes at room temperature. The mixture is diluted with ether and the organic phase is removed. The aqueous layer is brought to pH of approx. 3 with 2N HCl, and extracted with ether (3×). The combined acidic extracts are dried (MgSO$_4$) and evaporated. Crystallization of the residue from ethyl acetate/hexane yields 3-[(N-hydroxy-N-acetyl)aminomethyl]-6-phenoxy-2H-1-benzopyran, m.p. 153°–157° C.

EXAMPLE 7

Similarly to procedures described in examples herein are prepared:
a) N-hydroxy-N-methyl-6-benzyloxy-3,4-dihydro-2H-1-benzothiopyran-3-carboxamide;
b) 3-[(N-aminocarbonyl-N-hydroxy)aminomethyl]-6-methoxy-3,4-dihydro-2H-1-benzothiopyran; m.p. 153°-154° C.;
c) 3-[(N-acetyl-N-hydroxy)aminomethyl]-6-phenoxy-3,4-dihydro-2H-1-benzothiopyran;
d) 3-[(N-aminocarbonyl-N-hydroxy)aminomethyl]-6-phenoxy-3,4-dihydro-2H-1-benzothiopyran;
e) 4-[(N-aminocarbonyl-N-hydroxy)aminomethyl]-3,4-dihydro-2H-1-benzothiopyran;
f) 2-[(N-aminocarbonyl-N-hydroxy)aminomethyl]-3,4-dihydro-2H-1-benzothiopyran.

The 3,4-dihydro-2H-1-benzothiopyran-3-carboxylic acid starting materials can be prepared according to procedures described in the literature, e.g. U.S. Pat. No. 4,801,605 or Synthesis 1976, 409; 4-carboxylic acids can be prepared according to U.S. Pat. No. 4,305,955; 2-carboxylic acids can be prepared according to J. Org. Chem. 48, 881-883 (1983).

EXAMPLE 8

3-[(N-Aminocarbonyl-N-hydroxy)-aminomethyl]-6-phenoxy-2H-1-benzopyran (100 mg, 0.32 mmol) and 5% palladium on charcoal (106 mg) are suspended in 40 ml of ethanol and hydrogenated in a Parr shaker under $H_2$ pressure (45 psi) for 2 hours. The mixture is filtered through Celite and evaporated to dryness. The crude product is recrystallized from tetrahydrofuran/hexane to give 3-[(N-aminocarbonyl-N-hydroxy)aminomethyl]-6-phenoxy-3,4-dihydro-2H-1-benzopyran, m.p. 177°-178° C.

EXAMPLE 9

Similarly to procedures described in examples herein are prepared:
a) N-Hydroxy-N-methyl-6-phenoxy-3,4-dihydro-2H-1-benzopyran-3-carboxamide;
b) 3-[(N-aminocarbonyl-N-hydroxy)aminomethyl]-6-phenyl-3,4-dihydro-2H-1-benzopyran;
c) 3-[(N-acetyl-N-hydroxy)aminomethyl]-6-phenoxy-3,4-dihydro-2H-1-benzopyran;
d) 2-[(N-acetyl-N-hydroxy)aminomethyl]-3,4-dihydro-2H-1-benzopyran;
e) 2-[(N-aminocarbonyl-N-hydroxy)aminomethyl]-3,4-dihydro-2H-1-benzopyran;
f) N-hydroxy-N-methyl-3,4-dihydro-2H-1-benzopyran-2-carboxamide;
g) 4-[(N-aminocarbonyl-N-hydroxy)aminomethyl]-7-methoxy-3,4-dihydro-2H-1-benzopyran.

The 3,4-dihydro-2H-1-benzopyran-3-carboxylic acid starting materials can be prepared, e.g. according to procedures described in Eur. J. Med. Chem. 22, 539 (1987), by hydrogenation of the corresponding 2H-1-benzopyran-3-carboxylic acids. 3,4-Dihydro-benzopyran-2-carboxylic acid starting materials can be prepared according to procedures described in Eur. J. Med. Chem. 22, 539 (1987). For the preparation of compounds b) through e), and g) the acids are first converted to the corresponding alcohols with borane-THF complex.

EXAMPLE 10

A solution of 3-(N-hydroxyaminomethyl)-6-phenoxy-2H-1-benzopyran (0.41 g, 1.51 mmol) in 20 ml of 1,4-dioxane is treated with 0.28 g (2.15 mmol) of trimethylsilyl isothiocyanate. The mixture is heated at reflux for 30 minutes and allowed to cool. The mixture is diluted with water, and extracted with ethyl acetate (3×). The organic extracts are combined, dried (MgSO$_4$) and evaporated. Crystallization of the residual solid yields 3-[(N-aminothiocarbonyl-N-hydroxy)aminomethyl]-6-phenoxy-2H-1-benzopyran, m.p. 155°-160° C.

EXAMPLE 11

3-(N-hydroxyaminomethyl)-6-phenoxy-2H-1-benzopyran hydrochloride (1.95 g, 6.38 mmol) is suspended in 40 ml of acetonitrile, and treated with trimethylsilyl isocyanate (1.10 g, 9.57 mmol) under nitrogen. The mixture is heated at reflux for 1 hour and cooled to 0° C. The solid formed is collected by filtration, washed with ether and dried in vacuo to give 3-[(N-aminocarbonyl-N-hydroxy)aminomethyl]-6-phenoxy-2H-1-benzopyran, the compound of example 2(d), m.p. 168°-170° C. Crystallization from methanol: water yields pure compound having m.p. 178°-179° C.

The starting material is prepared as follows:

A mixture of 5-phenoxysalicylaldehyde (15.0 g, 70.0 mmol, see example 2d) and potassium carbonate (19.4 g, 140.0 mmol) in 250 ml of 1,4-dioxane is treated with acrolein (4.32 g, 77.0 mmol) under nitrogen. The mixture is heated at reflux for 6 hours. Water is added and the mixture is extracted with dichloromethane. The organic layer is dried (MgSO$_4$) and evaporated. The residue is purified by flash chromatography (silica gel, 10% EtOAc/hexane) to give 6-phenoxy-2H-1-benzopyran-3-carboxaldehyde, as a fluorescent solid.

The 6-phenoxy-2H-1-benzopyran-3-carboxyaldehyde intermediate can also be prepared as follows:

4-Phenoxyphenol (55.8 g, 300 mmol) is dissolved in 500 ml of acetonitrile. Potassium carbonate (43.5 g, 315 mmol), potassium iodide (12.6 g, 76 mmol) and propargyl chloride (24.6 g, 330 mmol) are added and the mixture is stirred at reflux overnight, cooled to room temperature and diluted with 100 ml of water. The mixture is extracted with ether (3×), and the combined ether extracts are washed with aqueous 1N NaOH (2×) and brine, dried (MgSO$_4$) and evaporated. Distillation of the residual amber oil gives 4-phenoxyphenyl propragyl ether; b.p. 136°-140° C./0.15 mm Hg.

4-Phenoxyphenyl propargyl ether (33.7 g, 150 mmol) in 50 mL of N,N-diethylaniline is added to refluxing (220° C.) N,N-diethylanile (300 ml) dropwise over a period of 10 minutes under nitrogen. The mixture is stirred at reflux for 8 hours, cooled and evaporated under high vacuum (bath temp. ~80° C.) to remove solvents. The residue is distilled to give 6-phenoxy-2H-1-benzopyran; b.p. 147°-150° C./0.5 mmHg.

6-Phenoxy-2H-1-benzopyran (3.36 g, 15 mmol) and N-formylmorpholine (10.4 g, 90 mmol) are dissolved in 10.5 ml of methylene chloride and treated with phosphorus oxychloride (13.8 g, 90 mmol) at 0° C. over 15 minutes. The mixture is then heated at 60° C. for 27 hours, cooled and poured slowly into an ice-water mixture. The mixture is then neutralized with aqueous ammonium hydroxide, and extracted twice with methylene chloride. The combined organic extracts are washed with water, dried (MgSO$_4$), and evaporated to give crude 6-phenoxy-2H-1-benzopyran-3-carboxaldehyde, which is used without further purification.

6-Phenoxy-2H-1-benzopyran-3-carboxaldehyde (5.00 g, 19.9 mmol) is dissolved in 175 ml of pyridine/ethanol (1:1) and treated with hydroxylamine hydrochloride (2.07 g, 29.7 mmol). The mixture is stirred for 1 hour and partitioned between ether and water. The aqueous layer is extracted with ether, and the ether layer is washed with 2N HCl, dried (MgSO$_4$) and evaporated to give 6-phenoxy-2H-1-benzopyran-3-carboxaldehyde oxime as a pale yellow solid.

Alternately, the oxime can be prepared as follows:

Sodium bisulfite (4.0 g) is added to a solution of 6-phenoxy-2H-1-benzopyran-3-carboxaldehyde (2.36 g, 9.37 mmol) in 40 ml of tetrahydrofuran and the mixture is stirred at room temperature for 4 hours. The precipitated product is collected, washed first with tetrahydrofuran and then with ether, and dried to yield the sodium salt of 6-phenoxy-2H-1-benzopyran-3-carboxaldehyde bisulfite adduct (the 3-α-hydroxymethylsulfonic acid).

A solution of 50% hydroxylamine in water (1.0 ml) is added to a suspension of 3.1 g of the above disulfite adduct in 30 ml of methanol. The reaction mixture is allowed to proceed for 2 hours with cooling, then diluted with 60 ml of water, and stirred for 2 hours with cooling. The precipitated product is collected, washed with water and dried to yield 6-phenoxy-2H-1-benzopyran-3-carboxaldehyde oxime.

The oxime (4.58 g, 17.1 mmol) is dissolved in 25 ml of dichloromethane and 25 ml of borane-pyridine complex (6.37 g, 68.5 mmol). The ice-bath is removed and the reaction is allowed to proceed for 2 hours at room temperature. This is again cooled to 0° C., and treated with conc. hydrochloric acid (26 ml). The resulting suspension is stirred at room temperature overnight. Dichloromethane is removed in vacuo, and the mixture is brought to pH 8 with ammonium hydroxide. Water is added and the mixture is extracted with ether. To the organic extract is added conc. HCl until acidic and the precipitate formed is collected, washed sequentially with ethanol and ether, and dried in vacuo. Recrystallization from ethanol or ethyl acetate: water, yields 3-(N-hydroxyaminomethyl)-6-phenoxy-2H-1-benzopyran hydrochloride as a white solid.

EXAMPLE 12 a) 3-(N-hydroxyaminomethyl)-6-methoxy-3,4-dihydro-2H-1-benzothiopyran (0.293 g, 1.3 mmol) is dissolved in 20 ml of 1,4-dioxane and treated with trimethylsilyl isocyanate (0.213 g, 1.85 mmol). The mixture is heated at reflux for 50 minutes, and cooled. This is then diluted with aqueous ammonium chloride, and extracted with ethyl acetate. The organic layer is dried (MgSO$_4$) and evaporated. The residue is triturated with ethyl acetate to give 3-[(N-aminocarbonyl-N-hydroxy)aminomethyl]-6-methoxy-3,4-dihydro-2H-benzothiopyran, m.p. 153°–154° C.

The starting material is prepared as follows: Borane-THF complex (1M in THF, 55.4 ml, 55.4 mmol) is cooled to 0° C. To this mixture is added 6-methoxy-3,4-dihydro-2H-1-benzothiopyran-3-carboxylic acid (6.1 g, 25 mmol) in 30 ml of THF dropwise. The cooling bath is then removed and the mixture is stirred overnight. This is quenched by addition of 50% aqueous acetic acid (8 ml), and concentrated in vacuo at 50° C. The residue is purified by flash chromatography (silica gel, 40% EtOAc/hexane) to give 3-hydroxymethyl-6-methoxy-3,4-dihydro-2H-1-benzothiopyran as an oil which crystallizes on standing.

The alcohol (3.43 g, 16.31 mmol) is dissolved in 150 ml of acetonitrile and treated with dibromotriphenylphosphorane (6.88 g, 16.31 mmol). The solvent is removed in vacuo, and the residue is triturated with ether. The solid is removed by filtration and washed with ether. The ether solution is concentrated and the residue is chromatographed (silica gel, 20% EtOAc/hexane) to give 3-bromomethyl-6-methoxy-3,4-dihydro-2H-1-benzothiopyran as an oil.

N,O-Bis-tert-butoxycarbonylhydroxylamine (1.18 g, 5.07 mmol) is dissolved in 10 ml of DMF and treated with sodium hydride (0.223 g, 60% in mineral oil, 5.58 mmol). After 30 minutes the above bromide (1.07 g, 3.90 mmol) in 10 ml of DMF is added dropwise, and the solution is stirred overnight. The mixture is diluted with ether and washed with aqueous ammonium chloride solution. The ether layer is dried (MgSO$_4$), and evaporated to yield crude 3-[(N-tert-butoxycarbonyloxy-N-tert-butoxycarbonyl)aminomethyl]-6-methoxy-3,4-dihydro-2H-1-benzothiopyran.

The above bis-t-butoxycarbonyl derivative (0.744 g, 1.75 mmol) is dissolved in 15 ml of dichloromethane and treated with 1 ml of trifluoroacetic acid. The mixture is stirred for 30 minutes at room temperature. The solvent is removed in vacuo and the residue is dissolved in ether. The organic layer is washed with 1N aqueous NaOH. The ether layer is then dried (MgSO$_4$) and evaporated to yield crude 3-(N-hydroxyaminomethyl)-6-methoxy-3,4-dihydro-2H-1-benzothiopyran.

b) Using the sequence of reactions under a) and starting with 7-methoxy-2H-1-benzopyran-3-carboxyaldehyde, 3-[(N-aminocarbonyl-N-hydroxy)aminomethyl]-7-methoxy-2H-1-benzopyran and 3-[(N-aminocarbonyl-N-hydroxy)aminomethyl]-7-methoxy-3,4-dihydro-2H-1-benzopyran, m.p. 169°–172° C., are obtained.

EXAMPLE 13

3-N-Hydroxyaminomethyl-6-(p-fluorophenoxy)-2H-1-benzopyran hydrochloride (14.05 g, 43 mmol) is treated with 250 ml of 1N NaOH and extracted three times with ether. The combined ether extracts are dried (MgSO4) and evaporated to give the corresponding free hydroxylamine. This is dissolved in 250 mL of dioxane and treated with methyl isocyanate (3.71 g, 65 mmol), and heated at reflux for 1 hour. The reaction mixture is cooled, treated with aqueous saturated ammonium chloride solution, and extracted three times with ethyl acetate. The combined organic extracts are dried (MgSO$_4$) and evaporated. The residue is crystallized from acetonitrile to yield 3-[{N-(N'-methylaminocarbonyl)-N-hydroxy}amino-methyl]-6-(p-fluorophenoxy)-2H-1-benzopyran, m.p. 171°–172°, of example 5(f).

A second product is crystallized from the acetonitrile mother liquor, and then recrystallized from acetonitrile to yield 3-{N-(N'-methylaminocarbonyloxy)-N-(N''-methylaminocarbonyl)}aminomethyl-6-(p-fluorophenoxy)-2H-1-benzopyran, m.p. 178°–179° C., the compound of formula III wherein R=6-p-fluorophenoxy; n=1; A=a direct bond; R$_1$, R$_2$, R$_6$ and R$_7$=H; X and Y=O; R$_3$=methylaminocarbonyl, R$_5$=methylamino, and the dotted line represents a bond.

The starting material is prepared from 4-(p-fluorophenoxy)-phenol according to processes described in examples 2(d) and 11.

4-(p-Fluorophenoxy)-phenol is prepared e.g. according to U.S. Pat. No. 3,652,665.

EXAMPLE 14 a) Preparation of 10,000 tablets each containing 20 mg of the active ingredient, having the formula as follows:

| | |
|---|---|
| 3-[(N-aminocarbonyl-N-hydroxy)aminomethyl]-6-phenoxy-2H-1-benzopyran | 200.00 g |
| Lactose | 2,535.00 g |
| Corn starch | 125.00 g |
| Polyethylene glycol 6,000 | 150.00 g |
| Magnesium stearate | 40.00 g |
| Purified water | q. s. |

PROCEDURE

All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 10-100 mg of one of the other compounds disclosed and exemplified herein.

b) Preparation of 1,000 capsules each containing 40 mg of the active ingredient, having the formula as follows:

| | |
|---|---|
| 3-[(N-aminocarbonyl-N-hydroxy)aminomethyl]-6-phenoxy-2H-1-benzopyran | 40.00 g |
| Lactose | 177.00 g |
| Modified starch | 80.00 g |
| Magnesium stearate | 3.00 g |

PROCEDURE

All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10–100 mg of the other compounds disclosed and exemplified herein.

What is claimed is:

1. A compound selected from the group consisting of
(i) a 3,6-disubstituted-2H-1-benzopyran of the formula:

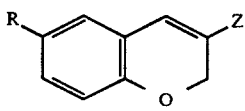

wherein
R is hydrogen, lower alkyl, halo, trifluoromethyl, lower alkoxy, phenyl, phenoxy, phenyl-lower alkoxy, or phenyl-lower alkyl, said phenyl, phenoxy, phenyl-lower alkoxy and phenyl-lower alkyl being unsubstituted or monosubstituted with lower alkyl, lower alkoxy, halo, cyano, or trifluoromethyl;
Z is

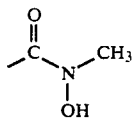

or

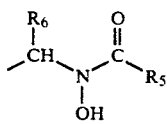

wherein
$R_5$ is methyl, amino, or mono-lower alkylamino; and
$R_6$ is hydrogen or methyl; and
(ii) a pharmaceutically acceptable salt of said benzopyran.

2. A compound according to claim 1 wherein in said benzopyran, R is phenoxy or benzyloxy, unsubstituted or substituted with halo or trifluoromethyl, $R_5$ is amino or methylamino, and $R_6$ is hydrogen.

3. A compound according to claim 2 wherein said benzopyran is selected from the group consisting of 6-benzyloxy-N-hydroxy-N-methyl-2H-1-benzopyran-3-carboxamide; 6-benzyloxy-3-[(N-aminocarbonyl-N-hydroxy)aminomethyl]-2H-1-benzopyran; 3-[(N-aminocarbonyl-N-hydroxy)aminomethyl]-6-phenoxy-2H-1-benzopyran; 3-[(N-aminocarbonyl-N-hydroxy)aminomethyl]-6-p-fluorophenoxy-2H-1-benzopyran; and 3-[(N-methylaminocarbonyl-N-hydroxy)aminomethyl]-6-p-fluorophenoxy-2H-1-benzopyran.

4. A compound according to claim 2 wherein said benzopyran is selected from the group consisting of 6-benzyloxy-N-hydroxy-N-methyl-2H-1-benzopyran-3-carboxamide; 6-benzyloxy-3-[(N-aminocarbonyl-N-hydroxy)aminomethyl]-2H-1-benzopyran; and 3-[(N-aminocarbonyl-N-hydroxy)aminomethyl]-6-phenoxy-2H-1-benzopyran.

5. A compound according to claim 1 which is 6-benzyloxy-N-hydroxy-N-methyl-2H-1-benzopyran-3-carboxamide or a pharmaceutically acceptable salt thereof.

6. A compound according to claim 1 which is 3-[(N-aminocarbonyl-N-hydroxy)aminomethyl]-6-phenoxy-2H-1-benzopyran or a pharmaceutically acceptable salt thereof.

7. A compound according to claim 1 which is 3-[(N-aminocarbonyl-N-hydroxy)aminomethyl]-6-p-fluorophenoxy-2H-1-benzopyran or a pharmaceutically acceptable salt thereof.

8. A compound according to claim 1 which is 3-[(N-methylaminocarbonyl-N-hydroxy)aminomethyl]-6-p-fluorophenoxy-2H-1-benzopyran or a pharmaceutically acceptable salt thereof.

9. A pharmaceutical composition suitable for inhibiting 5-lipoxygenase activity in mammals comprising an effective 5-lipoxygenase inhibiting amount of a compound of claim 1 in combination with one or more pharmaceutically acceptable carriers.

10. A method of inhibiting 5-lipoxygenase activity and of treating disorders in mammals which are responsive to such inhibition which comprises administering to a mammal in need thereof an effective 5-lipoxygenase inhibiting amount of a compound of claim 1 or of a said compound in combination with one or more pharmaceutically acceptable carriers.

11. A method according to claim 10 of treating inflammatory and allergic disorders.

* * * * *